(12) United States Patent
Olin et al.

(10) Patent No.: US 9,976,944 B2
(45) Date of Patent: May 22, 2018

(54) COLLECTION AND MEASUREMENT OF EXHALED PARTICLES

(75) Inventors: Anna-Carin Olin, Vastra Frolunda (SE); Ann-Charlotte Almstrand, Goteborg (SE); Jukka Lausmaa, Goteborg (SE); Evert Ljungstrom, Goteborg (SE)

(73) Assignee: PEXA AB, Gothenburg (SE)

( * ) Notice: Subject to any disclaimer, the term of this patent is extended or adjusted under 35 U.S.C. 154(b) by 975 days.

(21) Appl. No.: 12/680,428

(22) PCT Filed: Oct. 1, 2008

(86) PCT No.: PCT/SE2008/051110
§ 371 (c)(1),
(2), (4) Date: Aug. 17, 2010

(87) PCT Pub. No.: WO2009/045163
PCT Pub. Date: Apr. 9, 2009

(65) Prior Publication Data
US 2010/0297635 A1    Nov. 25, 2010

Related U.S. Application Data

(60) Provisional application No. 61/054,625, filed on May 20, 2008.

(30) Foreign Application Priority Data

Oct. 2, 2007 (SE) ...................................... 0702222

(51) Int. Cl.
*A61B 5/02* (2006.01)
*G01N 15/02* (2006.01)
(Continued)

(52) U.S. Cl.
CPC .......... *G01N 15/0255* (2013.01); *A61B 5/411* (2013.01); *A61B 5/097* (2013.01); *G01N 33/497* (2013.01); *G01N 2015/0261* (2013.01)

(58) Field of Classification Search
CPC ...................................................... A61B 5/097
(Continued)

(56) References Cited

U.S. PATENT DOCUMENTS 4,327,594 A * 5/1982 Nelson ........................ 73/863.22
5,042,501 A * 8/1991 Kenny et al. ................. 600/532
(Continued)

FOREIGN PATENT DOCUMENTS

JP       2001-108673      4/2001
WO       WO 96/28718      9/1996
(Continued)

OTHER PUBLICATIONS

"1 ToF-SIMS—An Overview" by John C. Vickerman, ToF-SIMS: Surface Analysis by Mass Spectrometry, pp. 1-40, Jan. 1, 2001.*
(Continued)

*Primary Examiner* — Jacqueline Cheng
*Assistant Examiner* — Vasuda Ramachandran
(74) *Attorney, Agent, or Firm* — Cermak Nakajima & McGowan LLP; Malcolm K. McGowan

(57) ABSTRACT

Particles are exhaled in the breath of animals. The nature and amounts of the particles can be indicative of certain medical conditions. They can therefore be collected, sorted according to size or mass and used in the diagnosis of one or more medical conditions. The invention provides a method and system for collecting and sorting exhaled particles and a method for diagnosis using said exhaled particles.

8 Claims, 7 Drawing Sheets

(51) Int. Cl.
  *A61B 5/00* (2006.01)
  *A61B 5/097* (2006.01)
  *G01N 33/497* (2006.01)
(58) Field of Classification Search
  USPC .......................................................... 600/543
  See application file for complete search history.

(56) References Cited

U.S. PATENT DOCUMENTS

| | | | |
|---|---|---|---|
| 5,787,885 A * | 8/1998 | Lemelson | A61B 5/4233 600/532 |
| 7,101,340 B1 | 9/2006 | Braun | |
| 2003/0008407 A1 | 1/2003 | Fu | |
| 2004/0046567 A1* | 3/2004 | Villinger et al. | 324/464 |
| 2004/0127808 A1* | 7/2004 | Vaughan et al. | 600/532 |
| 2004/0249300 A1* | 12/2004 | Miller | A61B 5/085 600/532 |
| 2005/0073683 A1* | 4/2005 | Gard et al. | 356/337 |
| 2005/0137491 A1 | 6/2005 | Paz et al. | |
| 2007/0167853 A1* | 7/2007 | Melker et al. | 600/532 |
| 2008/0038207 A1* | 2/2008 | Edwards | A61B 5/097 424/44 |

FOREIGN PATENT DOCUMENTS

| | | |
|---|---|---|
| WO | 02/082977 | 10/2002 |
| WO | WO2004/090534 A1 | 10/2004 |
| WO | WO 06/007180 | 1/2006 |
| WO | WO 2006/076265 | 7/2006 |
| WO | WO 07/089328 | 8/2007 |

OTHER PUBLICATIONS

"Valency of Antibody Binding to Enveloped Virus Particles as Determined by Surface Plasmon Resonance" by Hardy et al., Journal of Virology, vol. 77, pp. 1649-1652, 2003.*
"Airborne quartz concentration in an urban site" by Puledda et al., Environmental Pollution, V. 104, pp. 441-448, 1999.*
Chaplin, http://www.lsbu.ac.uk/water/hycel.html, 2006.*
Pharmacopeial Forum, vol. 30, Iss. 4, Jul.-Aug. 2004, pp. 1351-1360.*
Sensor Systems for Biological Agent Attacks: Protecting Buildings and Military Bases, by National Research Council (NAP), ISBN: 0-309-54832-2, 2005.*
Dekker Encyclopedia of Nanoscience and Nanotechnology, vol. 1, by Schwartz et al., p. 355, 2004.*
"Sensor Systems for Biological Agent Attacks: Protecting Buildings and Military Bases" by National Academies Press (NAP), ISBN: 0-309-54832-2, 2005.*
Edwards et al., "Inhaling to mitigate exhaled bioaerosols," Proc Natl Acad Sci USA, 2004,101(50):17383-17388.
Keskinen et al., "Electrical low pressure impactor," J. Aerosol Sci., 1992, 23(4):353-360.
Papineni and Rosenthal, "The size distribution of droplets in the exhaled breath of healthy human subjects," J Aerosol Med., 1997, 19(2):105-116.
Rosias et al., "Exhaled breath condensate in children: pearls and pitfalls," Pediatr Allergy Immunol., 15(1):4-19.
Russell et al., "Achieving high detection sensitivity (14 zmol) of biomolecular ions in bioaerosol mass spectrometry," Anal. Chem., 2005, 77:4734-4741.
International Search Report, in PCT/SE2008/051110, dated Jan. 26, 2009, 5 pages.
Written Opinion of the International Search Authority, in PCT/SE2008/051110, dated Jan. 26, 2009, 10 pages.
International Preliminary Report on Patentability, in PCT/SE2008/051110, completed Jan. 14, 2010, 10 pages.
Fennelly et al., "Cough-generated Aerosols of *Mycobacterium tuberculosis*, A New Method to Study Infectiousness," *Am J Respir. Crit Care Med*, 2004, 169:604-609.
Communication Pursuant to Rule 164(1) EPC and Supplementary Partial European Search Report for European Patent App. No. 08834965.9 (dated Nov. 16, 2017).

* cited by examiner

COLLECTION AND MEASUREMENT OF EXHALED PARTICLES

CROSS-REFERENCE TO RELATED APPLICATIONS

This application is a National Stage application under 35 U.S.C. § 371 and claims the benefit under 35 U.S.C. § 119(a) of International Application No. PCT/SE2008/051110, having an International Filing Date of Oct. 1, 2008, which claims the benefit of priority of the U.S. Provisional Application Ser. No. 61/054,625, having a filing date of May 20, 2008, and Swedish application 0702222-1 filed Oct. 2, 2007, all of which are incorporated herein in their entirety.

TECHNICAL FIELD

The present invention relates to particles which are exhaled in the breath of animals, particularly mammals, preferably humans. The nature and amounts of the particles can be indicative of certain medical conditions. They can therefore be collected, sorted according to size or mass and used in the diagnosis of one or more medical conditions.

BACKGROUND OF THE INVENTION

The human airways are daily confronted with at least 7-8 cubic meters of air and there is an advanced biological system to detoxify inhaled particles and gases. The first line defense against inhaled material is the Respiratory Tract Lining Fluid (RTLF), covering all the airways, among other thing containing several important antioxidant systems. Another important component of the RTLF is the surfactant, containing compounds for decreasing surface tension but also taking part in the innate immunity.

The composition of RTLF has been shown to change in inflammatory conditions of the airways. When the balance between anti-oxidants in RTLF and inhaled oxidants is disturbed, oxidative stress will initiate an inflammatory process. This inflammatory process, although very variable, is a major early event which is common in the development of most respiratory diseases, from asthma to lung cancer.

The patho-physiological processes leading to all respiratory diseases are so far not fully understood. One reason behind this is that those processes are difficult to monitor in humans. To evaluate the effect of for example various exposures, the available methods have been limited to measurement of lung-function, exhaled nitric oxide, induced sputum or analysis of broncho-alveolar lavage (BAL) or biopsies from bronchoscopy.

Those existing methods are either too invasive i.e. bronchoscopy, and thereby not applicable in larger studies which is warranted as susceptibility to different exposures are highly variable. Besides, both bronchoscopy and induced sputum are associated with certain risks, especially in sensitive populations as in those with pre-existing cardiopulmonary disease or asthma. Nitric oxide in exhaled air seems to a large extent solely to reflect an allergic inflammation and is therefore of limited value when studying other forms of airway disease. Lung function, on the other hand, is rather harmless to the studied patient but gives no information on underlying mechanisms of disease.

Other methods used include in-vitro studies, which only allow limited generalizations to the complex environment of human airways. The same is to a large extent true for animal studies, where—although genetic concordance to humans is high—the expression of various genes differs substantially.

Lately a new method has been introduced, namely, collection of exhaled breath condensate (EBC) i.e. exhaled water vapour that is condensed by the means of low temperature, where both volatile and non-volatile compounds have been identified. The non-volatiles found in EBC are believed to originate from particles formed within the airways. These particles are generated in the respiratory system while breathing, speaking or coughing and have been observed and, until now, studied mainly because such particles may serve as vehicles for transport of infectious material. How these particles are formed is still unknown, but a plausible mechanism may be through turbulent flow of the exhaled air in the central airways where the cross section area of the bronchi decreases substantially. A second hypothesis is that particles are formed from the RTLF when airways open up in the peripheral lung. In disease, the formation of particles may be enhanced due to increased turbulent flow and/or changed physical properties of the RTLF. An example of this is given in WO 02/082977.

The collection of exhaled breath condensate (EBC) is connected with a number of serious methodological difficulties such as dilution with water resulting in very low concentrations of the substances of interest, high contamination with substances originating from the oral cavity, high intra-individual coefficient of variation and a very inefficient way to sample the non-volatiles found in EBC.

Hence there is a need for better non-invasive methods to detect and monitor adverse health effects of the respiratory system. One, until now unexamined, way to overcome some of the methodological difficulties connected with analysis of EBC would be to directly sample and analyze the exhaled particles. The ability to determine amount and size of the collected particles will also give specific information about the status of the respiratory tract.

Measurement of Distribution of Particle Fractions of Different Sizes

There are only a few studies published examining exhaled droplets (i.e. particles).

Papineni and Rosenthal [*J Aerosol Med* 10(2):105-16] and Edwards et al. [*Proc Natl Acad Sci USA* 101(50):17383-8] measured a number of concentrations of exhaled particles in humans and described that it varied considerably between subjects but the concentrations were generally much lower than found in typical indoor air. Some information regarding size distributions of exhaled particles were also presented. It must be assumed that the main constituent of the droplets is water and thus, particle size should vary quickly with varying relative humidity (RH) of the surrounding air. The procedures to investigate the influence of RH used by Papineni and Rosenthal are not convincing since an IR-lamp was used to heat the air to change RH. Edwards et al. did not consider RH in a serious way in their investigation. Particle size was either invoked by indirect methods, e.g. microscopy of dried droplets or by light scattering methods with low size resolution. Thus, this state of affairs warrants further investigation of the variability in concentration and size distribution of exhaled aerosols.

There has also lately also been increasing interest in human aerosol formation mainly in the scope of the potential to detect their infectious potential. US 2005/0073683 and Anal. Chem. 2005, 77, 4734-4741 describe a real-time detection method and system for identifying preformed aerosol particles. The method described is aiming at detecting aerosols containing contagious material or "threat agents" on-line, by comparing their positive and negative mass-spectra with reference spectra which also will be developed. That method is not developed to diagnose or monitor human airway conditions and is markedly less sensitive which hinder detection of substances in very low concentrations, such as in the exhaled particles.

There is a lack of methods for easy monitoring of the airways. Invasive procedures, such as bronchoalveolar lavage and sputum induction, can be harmful to the patient and do not allow frequent sampling.

SUMMARY OF THE INVENTION

Measuring biomarkers in exhaled air is non-invasive and enables repeated sampling which can be useful for early detection of disease as well as monitoring of disease progression and therapy response. The technique has been successful for volatile substances, most importantly exhaled NO that is used as a marker for allergic asthma.

Non-volatile compounds are transported by aerosol particles that are believed to derive from the respiratory tract lining fluid. This is also confirmed by our preliminary data. These compounds may provide fundamental and specific information on patho-physiological processes in the airways. There are few studies on endogenous particles in exhaled breath. The mechanism and exact location of particle formation in the airways are unclear and a specific analysis of the chemical composition of particles has never been made.

A new technique has been developed for sampling and analysis of particles in exhaled breath. The method for determining the medical condition of a subject comprises the steps of:
a. collecting particles exhaled by said subject;
b. sorting said particles according to their mass or size, and
g. analysing the chemical content of said particles,
thus allowing the medical condition of said subject to be determined.

Additionally, the following steps may also be included in the method;
c. sorting said particles according to their mass or size to obtain a particle distribution profile of said particles;
d. comparing the particle distribution profile of the particles exhaled by said subject with a reference particle distribution profile;
e. noting similarities and/or deviations between the particle distribution profile of the subject and the reference particle distribution profile; and
f. assigning the deviations or similarities between the particle distribution profile of the subject and the reference particle distribution profile to one or more medical conditions in the subject; and optionally,
g. analysing the chemical content of said particles.

The medical condition may be selected from the group consisting of Asthma bronchiale, Cystic fibrosis, Chronic obstructive pulmonary disease (COPD), Interstitial lung-disease, Sarcoidosis, Pulmonary engagement in systemic disease such as systemic lupus erythromatodes (SLE), Pulmonary infections such as pneumonia, bacterial colonization or viral infections.

The reference particle distribution profile may be obtained from a subject not having a given medical condition, and step e. involves noting deviations between the particle distribution profile of the subject and the reference particle distribution profile. Alternatively, the reference particle distribution profile is from a patient having a given medical condition, and step e. involves noting similarities between the particle distribution profile of the subject and the patient, leading to the diagnosis of said given medical condition in the subject.

The invention also provides a method for providing a particle distribution profile of exhaled breath particles, said method comprising the steps of:
a. collecting particles exhaled by a subject; and
b. sorting said particles according to their size or mass to obtain a particle distribution profile of said particles.

In either method, the particles may be sorted according to their mass using an inertial impactor, or according to their size using a particle counter.

The impactor suitably has an inlet and an outlet, and comprising a plurality of stages arranged such that a gas stream (A) comprising particles (P) enters the impactor via the inlet and passes through each stage in turn before exiting the impactor via said outlet;
wherein each stage is separated from adjacent stages by a partition having an orifice which directs the gas stream (A) towards collection plates, the major face of each collection plate being arranged substantially perpendicular to the direction of flow of the gas stream (A);
whereby exhaled particles are passed through said inertial impactor in a gas stream (A); such that the primary gas stream (A) is directed towards each collection plates in each stage in turn; such that at least a first collection plate located in a first stage collects particles of a first mass and at least a second collection plate located in a second stage collects particles of a second mass.

After being sorted according to their size or mass, particles are analysed. They may be analysed by at least one analysis technique selected from the group consisting of: time-of-flight secondary ion mass spectrometry (TOF-SIMS), matrix assisted laser desorption ionization mass spectrometry (MALDI-MS), biochemical assays or protocols based on labelled antibodies, quantitative PCR analysis, scanning electron microscopy (SEM), gas-chromatography mass spectrometry (GC-MS), liquid chromatography mass spectrometry (LC-MS), surface plasmon resonance (SPR), fluorescence spectroscopy, TOC (total organic content) analysis, elemental analysis and inductively coupled plasma mass spectrometry (ICP-MS), with or without being first washed off the collection plates.

The invention also relates to a system for collecting and sorting exhaled particles, said system comprising:
a. a reservoir having first opening and a second opening;
b. a two-way mouthpiece connected to the first opening of the reservoir;
c. an inertial impactor having an inlet and an outlet, said impactor comprising a plurality of stages arranged such that a gas stream (A) comprising particles (P) enters the impactor via the inlet and passes through each stage in turn before exiting the impactor via said outlet;
wherein each stage is separated from adjacent stages by a partition having an orifice which directs the primary gas stream (A) towards collection plates, the major face of each collection plate being arranged substantially perpendicular to the direction of flow of the gas stream (A); the inlet of the inertial impactor being connected to the first opening of the reservoir.

The measurement and analysis of exhaled particles meets the following requirements:
Non-invasive
Enable repeated measurements in humans
Follow the kinetics of various patho-physiological processes in the lungs including anti-oxidant systems, protein expression, changes in lipid patterns and differences in particle size and concentration.
Platform for non-invasive identification of new biomarkers for diagnosis and monitoring of a) respiratory disease such as;
   Asthma
   Chronic obstructive lung disease
   Interstitial lung diseases
   Lung cancer
   Respiratory infections
   Pulmonary engagement in systemic disease such as SLE, scleroderma, and rheumathoid arthritis.
b) systemic diseases such as;
   Cardio vascular disease
   Diabetes
   Metabolic syndrome
   Hypercholesterolemia
Monitoring of intubated patients
Monitoring of exposure
Identify new targets for pharmacological treatments
Identify individuals with increased genetic susceptibility for certain exposure or disease

DETAILED DESCRIPTION OF PREFERRED EMBODIMENTS

Figure 1:
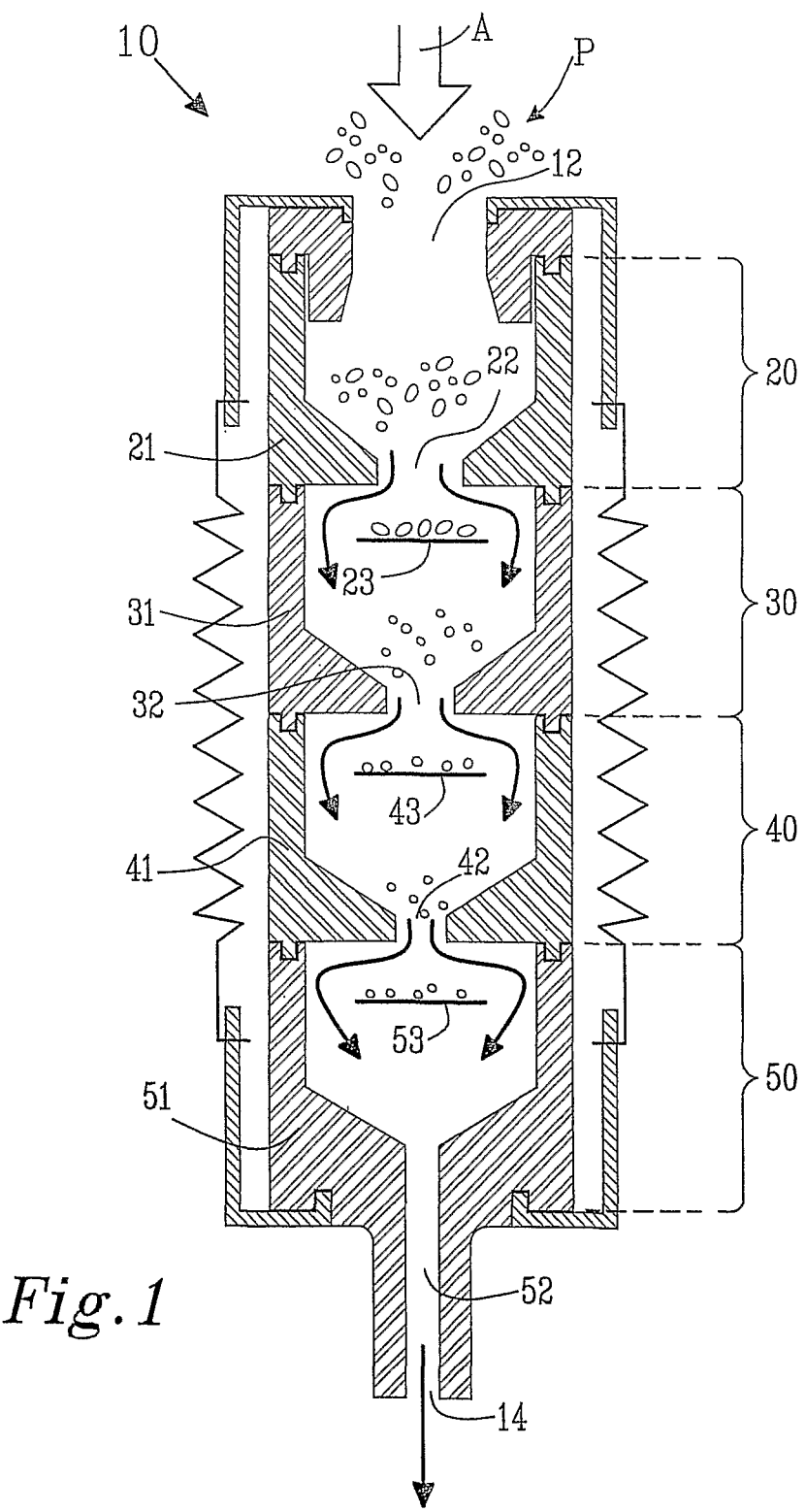
FIG. 1 illustrates an inertial impactor according to the invention.

In a first embodiment, the present invention relates to a method determining the medical condition of a subject. The word "determining" is understood in its broadest scope; i.e. the evaluation of the presence (qualitative) and/or extent (quantitative) of a medical condition. In addition, "determining" also refers to the determination of any predisposition a subject might have to acquire a given medical condition.

The term "medical condition" should not be understood as limited to diseases and disorders. It may be relevant to investigate the medical condition of healthy subjects in a non-diagnostic manner, for example in the following situations:
   subjects who may be under the influence of medication or drugs (e.g. doping tests), or otherwise exposed to chemical substances (e.g. pollutants, occupational hazards);
   subjects involved in physical activity or health programmes (e.g. to determine the fitness or health of a subject);
   healthy subjects who might have a predisposition to develop a certain disease or disorder.
   healthy subjects who might have a genetic susceptibility to develop a certain disease or disorder or for less tolerance for specific exposures.
Subjects to which the method of the invention can be applied are animals, particularly mammals, preferably humans. The invention will primarily be described with reference to humans.

In a second embodiment, the present invention provides a method for providing a particle distribution profile of exhaled breath particles.

The first step in both methods of the invention involves collecting particles exhaled by a subject. A single exhalation may provide a sufficient number of particles, although typically, particles are collected from repeated exhalations. For the diagnosis of medical conditions in humans, for example, particles might be collected from continuous inhalation/exhalation for a period of time comprising one single exhalation up to several tens of minutes, e.g. between 1 second and 100 minutes, such as between 1 second and 50 minutes, between 5 seconds and 20 minutes or between 10 seconds and 5 minutes.

By varying the exhalation pattern, it may is also possible to collect particles which are representative from different portions of the respiratory tract. A forced exhalation is increasing the turbulent flow when the airways narrows and hence increasing the particle production in the somewhat more central airways in contrast to normal breathing where presumably more particles are formed by airway opening from the most distal parts of the airways.

After collection, the particles are sorted according to their mass or their size. A particle counter may be used to count individual particles and thus provide a number-size distribution of particles. Mass distribution may be calculated by assuming spherical particles and a density. Advanced chemical analysis of the collected non-volatile material may ensue (as detailed below).

Sorting the particles according to their mass or their size may also provide a particle distribution profile of said particles. The particle distribution profile is a measure of how many particles of a particular mass or size (or mass or size range) are present in the exhaled air, and can also be used to determine the medical condition of a subject. By particles in this context is meant solid, liquid and liquid-coated solid objects, which are often suspended in a gas, normally but not necessarily air. Object sizes normally but not necessarily being larger than 0.005 micrometer and normally but not necessarily being smaller than 15 micrometer. By size is meant either aerodynamic diameter or electrical mobility diameter, suitably aerodynamic diameter.

FIG. 1 shows an inertial impactor 10 used to collect exhaled particles (shown as P in FIG. 1). The impactor 10 is a container having an inlet 12 through which gas and exhaled particles may enter the impactor 10, and an outlet 14 through which gas and exhaled particles may leave the impactor 10. The impactor 10 in FIG. 1 has been illustrated as a cylinder, with inlet 12 and outlet 14 on opposing circular faces of the cylinder; however, other geometries and arrangements of the inlet and outlet 12, 14 are possible.

The impactor 10 comprises a plurality of stages 20, 30, 40, 50. FIG. 1 illustrates four stages 20, 30, 40, 50, although impactors with from 2 to 15 stages are known. A primary gas stream (A) comprising particles (P) enters the impactor 10 via the inlet 12 and passes through each stage 20, 30, 40, 50 in turn before exiting the impactor 10 via the outlet 14. The primary gas stream (A) comprises air and particles exhaled by a subject. The flow is caused by a pump connected to the outlet of the impactor. Typically, according to the invention, the exhaled air and particles are not modified between leaving the subject and entering the impactor.

Each stage 20, 30, 40, 50 is separated from adjacent stages by a partition 21, 31, 41, 51. Each partition has at least one orifice 22, 32, 42, 52 (in practise, a plurality of orifices is present in each partition) which directs the gas stream (A) towards collection plates 33, 43, 53. The major face of each collection plate 33, 43, 53 is arranged substantially perpendicular to the direction of flow of the gas stream (A).

The collection plates 33, 43, 53 used have a thickness of around 1 mm and are square with 10-12 mm side. The plates are held in place on the substrate holders by double sided tape at the exit of the air streams through the nozzles. The plates are made of elemental silicon since this is favourable for the ensuing analysis. The plates must be extremely clean since trace amounts of impurities may interfere with the ensuing analysis of the particles. The cleaning of the silicon plates may be done in several ways, preferably by ultrasonic cleaning in organic solvents followed by UV-ozone treatment, or by immersion in 1-10% nitric acid or hydrogen peroxide.

After cleaning, the preparation of the collection plate surfaces can be further optimized with respect to the collection and the ensuing chemical analysis. By varying the hydrophilicity or other surface chemical properties of the collection plates, the interaction of the particles with the surface may be controlled in a favourable way. Preferably, the entire surface of the collection plate is modified. A hydrophobic collection surface will bind hydrophobic moieties such as the hydrocarbon chains of lipids molecules more strongly than a hydrophilic surface. The normally hydrophilic silicon surfaces can be made hydrophobic by coating with a thin layer of hydrophobic substance such as methyl silanes, or by coating the silicon substrate with gold and then applying a monolayer of methyl terminated thiols onto the gold. Similarly, the collection surface can be made to specifically bind certain molecules. Specific proteins can be made to bind to the collection plate surface by coating it with antibodies for the proteins in question. By using the proper reagents, the binding of the analyte can induce a colour change or emission of fluorescent light, which can be detected in situ and in real time. In situ detection can also be done with an electric measurement of the current or capacitance change induced by the binding of the analyte to the surface of the collection plate. In this case the collection plate also has the necessary electrical connections that enable such a measurement. The impactor can comprise the necessary electrical connections which make contact with appropriate connections on the collection plate.

Particles with inertia such that they are unable to follow the air stream when it is deflected around the first collection plate 33, will impact the collection plate 33 while particles with less inertia will continue to the next stage 40. The inertia of a particle depends on its mass that, in turn, depends on its size. In this way, mass or size-segregation of the particles is possible.

Thus by choosing the number of orifices, their diameter and the distance from orifice to collection plate in each stage, it is possible to achieve mass or size segregation of the particles in an aerosol. Particles with high inertia, i.e. large mass/size will be separated on the early stages while particles with less inertia, i.e. smaller mass/size will impact on the later stages. By choosing the shape of the orifices, it is possible to concentrate the collected material in forms suitable for the ensuing chemical analysis. The increase in concentration of the material on the collection plates, compared with the exhaled air or the breath condensate, is considerable.

In the present case, a modified 3-stage Dekati PM10 was used. The modifications consisted of reducing the number of nozzles of the third stage by a factor of two and increasing the design flow rate of the impactor by a factor of 1.5.

The original impactor was a 10 liter per minute variety that was operated at a flow of 15 liters per minute. The 20 orifices of the last stage were reduced to 10 thus increasing the gas velocity in each nozzle by a factor of 2. The 50% cut-off size [i.e. half the number of particles of that size are collected while half the number continues. This does not show a step-like collection characteristic, rather an “S-like” characteristic] were 7, 1.5 and 0.5 μm for the three stages, respectively.

The surface functionalization of the collector plate, as described above, can be miniaturized, to achieve different functionalizations at each nozzle, in order to facilitate optimal parallel collection different analytes. Similarly, parallel in situ optical or electrical detection of specific substances can be done by a collection plate chip, in which the appropriate surface functionalizations and/or electrical connections have been supplied to the collector plate at the location of the nozzle exits.

The impactor is designed to collect the exhaled particles in an as efficient as possible way. This implies that virtually all particles present in the exhaled air, in a given mass/size interval, are collected for analysis. The particles are recovered in a concentrated form suitable for advanced chemical analysis.

The invention also provides a system 100 for collecting and sorting exhaled particles, said system comprising:

a. a reservoir 114 having first opening 112 and a second opening 113;

b. a two-way mouthpiece 110 connected to the first opening 112 of the reservoir 114;

c. an inertial impactor 10 having an inlet 12 and an outlet 14, said impactor 10 comprising a plurality of stages 20, 30, 40, 50 . . . arranged such that a gas stream (A) comprising particles (P) enters the impactor 10 via the inlet 12 and passes through each stage 20, 30, 40, 50 . . . in turn before exiting the impactor 10 via said outlet 14;

wherein each stage 20, 30, 40, 50 . . . is separated from adjacent stages by a partition 21, 31, 41, 51 . . . having an orifice 22, 32, 42, 52 . . . which directs the primary gas stream (A) towards collection plates 33, 43, 53 . . . , the major face of each collection plate 33, 43, 53 . . . being arranged substantially perpendicular to the direction of flow of the gas stream (A); the inlet 12 of the inertial impactor being connected to the first opening 112 of the reservoir 114.

The collection system may be set up as is illustrated in FIG. 2. The greater part of the system is located in a thermostatted compartment 120. The individual from whom exhaled particles are desired inhales room air through a two-way mouthpiece (110). Upon inhalation, the inhaled air (A) passes a high efficiency particle filter (125) located before the mouthpiece.

The mouthpiece (110) is kept at a temperature such that the size distribution of the exhaled aerosol is not changed either by evaporation or condensation of water vapour. The exhaled air (A) passes the mouthpiece (110) into a system located in a thermostatted compartment (120), also here with the purpose of maintaining the aerosol size distribution. In the compartment is located a reservoir (114) for the exhaled air. Further, a particle counter (116) is connected to the first opening (112) of the reservoir (114) to count and measure particle size. An inertial impactor (10) for the collection of particles (P) is also connected to the reservoir first opening (112).

The flow through the impactor (10) is typically maintained by a pump (115), located outside the thermostatted compartment. FIG. 2 also shows gas discharge (130) and that particle-free humidified air is added (135).

A particle counter (116), capable of measuring number-size distributions, supplies additional important information. The particle counter used here is a Grimm 1.108 optical particle counter (Grimm Aerosol Technik, Ainring, Germany), capable of counting, and sizing particles in 15 size intervals from 0.3 to 20 micrometer. The instrument may provide a number size distribution of the measured aerosol or a mass distribution, calculated from the measured number size distribution. In the instrument, the particle-laden air is passed through a small, well defined, intensely illuminated volume in a manner so that only one particle at a time is illuminated. The illuminated particle gives rise to a pulse of scattered light, the intensity of which is measured. Since the intensity of scattered light depends on the particle size, it is possible to count and size the particles in the air stream.

The reservoir (114) acts as a buffer where the exhaled air is stored when the flow of exhaled air exceeds the combined impactor (10) and particle counter (116) flows. The reservoir (114) supplies air to the impactor (10) and particle counter (116) when no exhalation is taking place. Moist, particle-free air is added at the second opening (113) of the reservoir (114) so that there is always a positive discharge flow. The flow is measured by a flow meter (119) located at the discharge end of the reservoir (114). By displaying the flow graphically in real time, it is possible for the subject to control breathing frequency and intensity according to instructions.

A sample is taken in the following way. It is assumed that the impactor is loaded with clean collection plates, and that the system, especially the impactor, has attained the desired temperature. First, the flow meter is zeroed to allow a proper measurement of flows, then the moist clean air flow is set at a value so that a positive flow will be maintained from the system during measurement. Then the impactor flow is set at a value lower than the clean air flow. During this procedure, no deposit will be collected on the plates, since the system is fed by clean particle free air. Then the optical particle counter is started and it is checked that no spurious particles are present, e.g. indicating a leak into the system. Exhalation into the system then begins, the particle counter continuously draws a sample and produces a size distribution every six seconds while the impactor collects samples for later analysis. When a required amount of sample has been obtained, the collection is terminated, the time of sampling and exhaled volume recorded. The flow through the impactor is turned off, the impactor removed from the measurement system and the loaded plates are recovered.

In that two components of the system are "connected", it is to be understood that air and exhaled particles can flow between the components. Connection is usually made by tubes, with appropriate junctions, valves or seals to direct gas/particle flow.

One possibility this system enables is a quantification of particle formation in different fractions at different exhalation rates. This may be a very easy way to detect turbulent airflow, as for example in asthma, and may be used as marker for disease.

Analysis

The collection plates 23, 33, 43, 53 and their associated particles P can be removed from the impactor 10 and the particles can be analyzed as to their chemical content. The chemical content of the particles P provides an insight into the medical condition of a subject (as is described below in the section entitled Medical Conditions).

In one analysis strategy, the particles are analysed while still on the collection plates. This is done with the following chemical analysis techniques that provide complementary information about specific substances present in the particles. Time-of-flight secondary ion mass spectrometry (TOF-SIMS) is especially useful for analysis of substances in the mass range up to 1000 u, in particular various types of lipids, for which the profiles will change during various disease conditions. Matrix assisted laser desorption ionization mass spectrometry (MALDI-MS) is a suitable method for analysing peptides and larger macromolecules (various proteins), that are associated with imflammatory responses. The MALDI-MS identification of proteins can be further facilitated by applying proteolysing enzymes, preferably trypsin, that will dissociate the proteins into segments that can be determined and used for conclusive protein identification by comparison with publicly available data bases. Analysis of specific proteins or other biomolecules (e.g. DNA) can also be done by applying different biochemical assays or protocols based on labelled antibodies, directly to the collection plates. Scanning electron microscopy (SEM) can be used for analysing the morphology of the collected particle aggregates. Such an analysis can reveal particles of non-biological origin, for example, particles due do exposure of the subject.

In another analysis strategy, the collected material is removed (washed off) from the collection plates. The washing solution containing the collected particles can then be further processed for different chemical or biochemical analysis techniques. In the simplest analysis, the total amount of organic material in the collected particles can be analysed with a TOC (total organic content) analyser. Different elemental analysers can be used for obtaining the amounts of carbon, nitrogen, oxygen and sulphur in the collected material, which in turn reflects the relative amounts of different classes of biomolecules (lipids, carbohydrates, proteins). Trace amounts of inorganic elements, especially metals, can be determined by inductively coupled plasma mass spectrometry (ICP-MS). Such an analysis will provide information not only about substances of non-biological origin, but can also be used to detect metal-containing biomolecules (proteins) of importance in specific disease conditions, for example iron-response protein (IRP). Cu and Zn have also been shown to be increased in lung tumor tissue, and seem both of importance modulating the inflammatory response in the airways. For more biomolecule specific analyses, the three techniques gas-chromatography mass spectrometry (GC-MS), liquid chromatography mass spectrometry (LC-MS), and direct MALDI-MS, will provide complementary information. GC-MS will provide information about semi-volatile substances in the mass range up to around 500 u. LC-MS will provide qualitative and quantitative information about different biomolecules, such as lipids, peptides and proteins as well as their modifications. Direct MALDI-MS, finally, can be used for pattern detection of biomolecules up to several 10 000 u. allowing one detection and identification of both lipid and protein profiles. The collected and washed off material can also be subjected to biochemical analyses, in particular labelled antibodies for specific proteins of interest, or quantitative PCR analysis for analysis of genetic material.

There are several techniques to facilitate the sample handling and to increase the sensitivity of the method. One advantage already present in the method is the possibility to directly analyze the collection plate taken from the impactor using surface desorption mass spectrometric techniques. A further advantage would be to purify the sample and/or modify it directly on the plate with for example the enzymes mentioned above, so called on-plate digestion. It is also possible to create different kinds of surfaces on the collection plate which have been covalently modified with receptor molecules or enzymes for direct binding or modification of specific analytes in the particle sample. These methods are well known and can easily be applied in an organic laboratory. This will speed up the analytical process considerably making it more feasible for investigations of large patient groups.

After the identification of novel biomarkers by mass spectrometric methods is it possible to introduce new analytical instruments such as surface plasmon resonance (SPR) and fluorescence spectroscopy in order to easily scale up the analysis to large population groups. These two methods are more easily used by non-experts which makes the particle collection method more accessible for use at hospitals and health care centres and will also make studies of large patient groups more time efficient. It is very advantageous to be able to use the collection plate directly from the impactor.

The different mass spectrometric (MS) techniques mentioned above have the distinct advantage that they provide global information about the composition of the collected particles. This means that by combining different MS techniques, the majority of biomolecules will be possible to detect in a non-predetermined way. This is in contrast to many other biochemical analysis techniques, which only detect pre-selected and labelled substances. The compatibility of the present method with MS techniques is thus an important advantage for identifying new specific biomarkers for different diseases.

The analysis of the particles may be compared with a reference chemical analysis, and deviations and/or similarities from the reference chemical analysis can be identified. This can be used in determining one or more medical conditions in the subject. The reference chemical analysis can be from subjects having a certain medical condition (in which case similarities in the chemical analysis are looked for) subjects not having a certain medical condition (in which case deviations in the chemical analysis are looked for), or from the subject themselves, yet taken under different circumstances (e.g. at a later point in time, or after a certain course of treatment or exercise).

A particle distribution profile can be determined by sorting the particles on each collection plate. The particle distribution profile obtained can be used in determining one or more medical conditions in the subject. If diagnosis is to be made, the particle distribution profile of the particles exhaled by the subject is compared with a reference particle distribution profile. Similarities and/or deviations between the particle distribution profile of the subject and the reference particle distribution profile are noted and the deviations or similarities between the particle distribution profile of the subject and the reference particle distribution profile are assigned to one or more medical conditions in the subject.

The reference particle distribution profile may be a particle distribution profile from a subject not having a given medical condition. In this case, deviations may be noted between the particle distribution profile of the subject and the reference particle distribution profile, providing an indication of a medical condition.

The reference particle distribution profile may alternatively be from a subject having a given medical condition. Similarities can then be noted between the particle distribution profile of the subject and the patient, leading to the diagnosis of said given medical condition in the subject.

The reference particle distribution profile may also be from the subject themselves, yet taken under different circumstances (e.g. at a later point in time, or after a certain course of treatment or exercise). This would allow the monitoring of a medical condition by the method of the present invention.

Medical Conditions

Medical conditions which may be determined or monitored by the present invention include
Asthma bronchiale
Cystic fibrosis
Chronic obstructive pulmonary disease (COPD)
Lung cancer
Interstitial lung-disease
Sarcoidosis
Pulmonary engagement in systemic disease such as systemic lupus erythromatodes (SLE)
Pulmonary infections
   pneumonia
   bacterial colonization
   viral infections
It is plausible that also other systemic medical conditions can be monitored such as
Heart failure (for example endothelin-1)
Hypercholesterolemia (cholesterol is found in the exhaled particles)
Diabetes (insulin is found in the particles)
Metabolic syndrome
Increased genetic susceptibility to disease or exposure The particles may comprise or consist of biomarkers which are indicative of specific medical conditions. The method according to the invention allows the detection of such biomarkers.

The exhaled particles are believed to originate from the respiratory tract lining fluid (RTLF) covering the entire respiratory epithelium [*Pediatr Allergy Immunol* 15(1):4-19] containing large quantities of antioxidants and surfactant. One should also keep in mind that the constituents of the RTLF changes from the proximal to the distal airways.

One substance that is abundantly present in the RTLF is Clara cell protein 16 (CC16), also acting as an anti-inflammatory protein, produced by the Clara cells. CC16 has until now only been measured in BAL and blood. Other substances that so far have gained interest are surfactant proteins A-D, also only measured in bronchoalveolar lavage, BAL.

Of special interest is the detection and monitoring of concentrations of anti-oxidants in the particles. A potential biomarker is glutathione which is in high abundance in the respiratory tract. Other anti-oxidants that are potential biomarkers in the exhaled droplets are the metal-binding proteins ceruloplasmin and transferinn which are likely to be detected with matrix assisted laser desorption/ionization mass spectrometry (MALDI MS). Additional potential antioxidants with low molecular weight, for example ascorbate, α-tocopherol, urate and L-cystein is also likely to be detected with mass spectrometric methods, these molecules are also biomarkers for oxidative stress.

Potential biomarkers that are directly involved in oxidative stress as antioxidants are: glutathione, ceruloplasmin, transferin, ascorbate, α-tocopherol, urate and L-cystein. Glutathione is especially interesting since it is highly abundant in the airways. The analytical methods that will be used to detect these antioxidants will be mass spectrometry.

a. Lipids

The profile of phospholipids in RTLF may serve as biomarkers for disease. Alterations in phospholipid composition (PC) have been seen in most airway diseases, such as acute respiratory distress syndrome (ARDS), pneumonia, cystic fibrosis and asthma. In asthma, PC was decreased in BAL and the relation between PC/phosphatidylglycerol (PG) has been shown to change after allergen challenge.

A new emerging research-area in respiratory disease is also the nitration and oxidation of lipids, which may alter their functions.

Surfactants, comprising phospholipids and proteins, in the RTLF are believed to serve important functions in the innate immune system. The phospholipids are precursors for a variety of cytokines active in the innate immunity such as prostaglandins, thromboxanes. eotaxins, lipoxins, resolvins etc. The surfactant proteins have also been shown to play an important role in the innate immunity, among other things acting as antigen-presenting cells and regulatation of cell death. The knowledge of metabolism of surfactant is until now very limited but believed to be important to understand pathogenesis of respiratory disease.

Surface analysis of the silicon collection plates with TOF-SIMS has revealed a wide range of phospholipids in the exhaled particles. The phospholipids detected in particles are in agreement with phospholipids found in RTLF in BAL studies. The relative amounts of phospholipids are also in agreement with BAL. The relative amounts of phospholipids are also in agreement with BAL. The ratio of $CN^-$+ $CNO^-$ (fragments presumably coming mainly from proteins and peptides) to $PO_3^-$ was elevated among patients with asthma and patients with cystic fibrosis. This ratio may reflect a plasma protein leakage into the airspaces owing to airway disease.

b. Proteins and Peptides

Proteomic analysis of bronchoalveolar lavage has revealed a multitude of proteins present in the sample. The analysis has been performed using 2D gels and mass spectrometry. Proteins involved in, among other things, imumunoinflammatory processes, cell growth, oxidant-antioxidant and protease-antiprotease systems as well as proteins with unknown functions. For example proteomic studies of BAL have been performed on allergic asthmatic patients. In this study, 1592 proteins were identified and 160 of these were expressed differently in the patients compared with a control group. The most abundant proteins are plasma proteins that probably are derived from diffusion from the blood-air barrier. An increase in plasma proteins is probably due to exudation or damage. It is very likely that several of the peptides and proteins detected in BAL are also present in the exhaled particles.

Peptides and proteins that are biomarkers for diseases in the airways include endothelin-1, Interleukin-4, Interferon-g, surfactant protein A-D and Clara cell protein 16. These molecules can be detected with ESI-MS and MALDI-MS or by immuno-assays. There is a high probability that more types of biomarkers will be detected in the present invention, since the collection of particles is more efficient than using exhaled breath condensate where a smaller number of particles are collected. Treating the proteins in the collected samples with proteolytic enzymes such as trypsin will result in several peptide fragments which will give rise to a pattern, unique for a specific protein set.

Investigation of posttranslational modifications such as phosphorylation and glycosylation of proteins are also potential targets for biomarkers. Wrong phosphorylation patterns are known to be a part of several diseases.

Another important class of biomarkers in the respiratory tract is mucin glycoproteins which contribute to the mucociliary defense that protects the airways against pathogens and environmental toxins. For patients with asthma, COPD and cystic fibrosis is there an overproduction of mucin glycoproteins. Although there are some difficulties with analysis of glycoproteins due to their variable glycosylation pattern is it still valuable to pursue this group of compounds due to their involvement in different respiratory diseases. An advantage in analyzing glycoproteins is their easy purification by affinity chromatography. Furthermore, it is probable that variations in observed protein glycosylation patterns will be disease related, and therefore should be considered as a potential biomarker.

c. Cellular Material and Gene Expression

It is likely that the exhaled particles contain cells or cell structures containing substances with genetic information, in particular DNA and RNA. This cell material may be due to bacteria, viruses, or cells of the respiratory tract. Analysis of the genetic expression of such material can either provide new information about the pathology of, or be used as a highly specific and sensitive means of diagnosing specific diseases. The method could hence be used to identify the pathogen in diseases such as pneumonia and exacerbations of COPD, but also for early detection of for example colonization with *Pseudomonas aeruginosa* in cystic fibrosis, which often is a clinical problem.

d. Metals

It has been possible to trace exposure to metals in the EBC, such as iron, cadmium, lead, aluminium, copper. The metals are most probably transported to the EBC bound to exhaled particles. This implies that the method also has a potential to monitor exposure to various components of air-pollution, such as iron, zinc, cadmium or aluminium. Exposure to metals in ambient nano-particles have also been linked to the development of respiratory disease.

EXAMPLES

Exhaled particles from four healthy subjects were collected on silica wafers. The concentration of particles was recorded by means of an optical particle counter (Grimm 1.108). Forced exhalations (with nose clips) were performed in order to obtain a high particle production. The subjects were trained to perform repeated consecutive exhalations corresponding to 80% of their individual maximal forced expired volume in one second (FEV1). A deviation of 10% from the target flow was considered acceptable. Sampling was performed during 15 minutes in the morning of day 1 and repeated in a similar way day 2.

The chemical composition of exhaled particles on the silica wafers were analyzed using Time-of-Flight secondary ion mass spectrometry (TOF-SIMS IV IONTOF GmbH). A 25 keV $Bi^{3+}$ primary ion was rastered over an area of 500×500 $\mu m^2$ centered around the spot with particles. Mass spectra of positive and negative secondary ions were recorded with the instrument optimized for maximum resolution. Spectra from the total analysis area or from selected regions of interest, and images for selected ions were extracted from the recorded raw data files using the instrument software. Assignment of the peaks in the spectra was done by comparison with reference spectra from pure substances and from published data from other mass spectrometry methods, and the assignments were also controlled by comparison with theoretical isotope patterns. The relative intensities of the identified peaks were calculated by normalization against total ion intensities in respective spectrum.

Figure 3A:
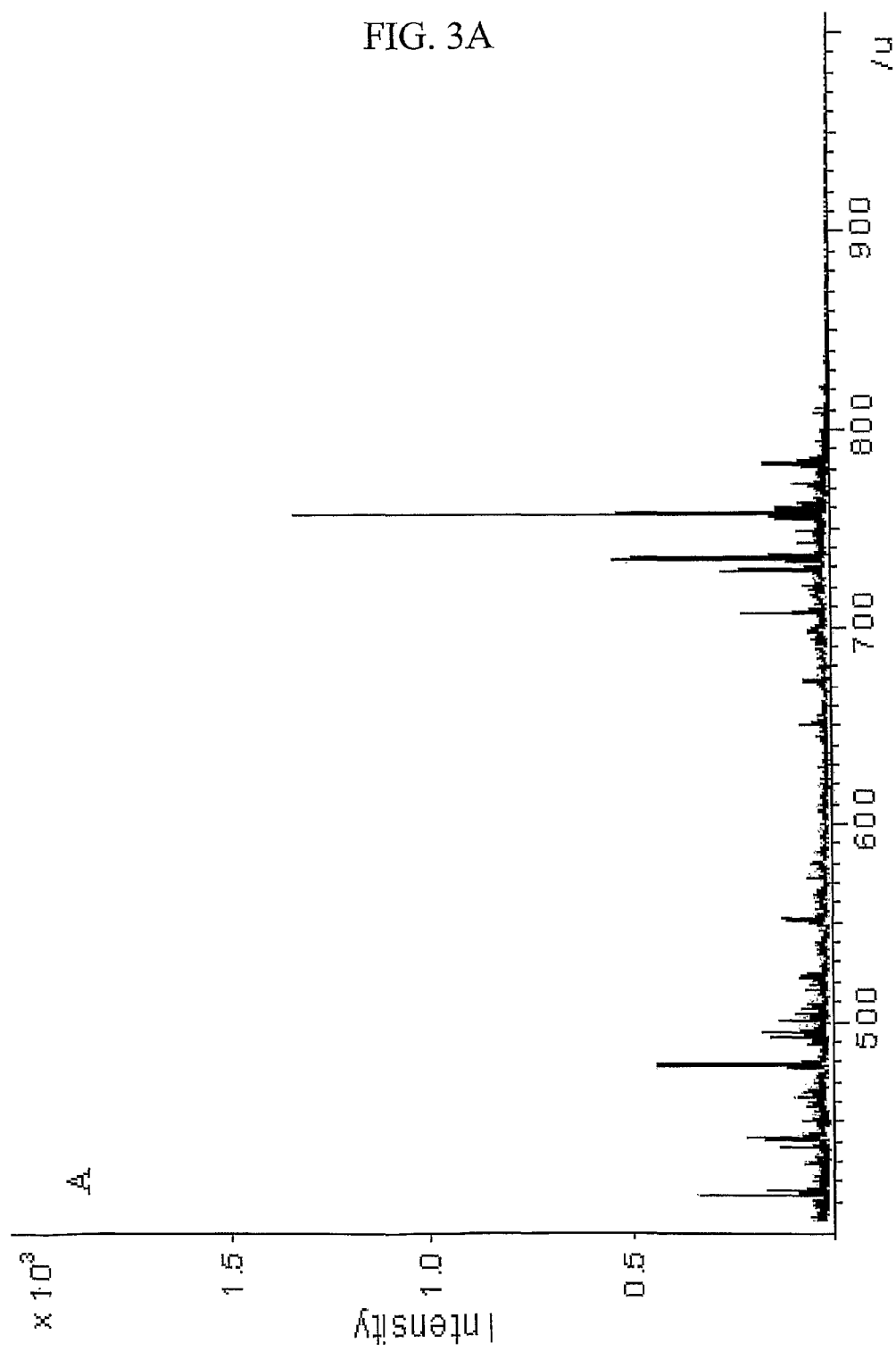
FIG. 3 shows positive (FIG. 3A) and negative (FIG. 3B) TOF-SIMS spectra of a particle spot from one control subject.
Figure 3B:
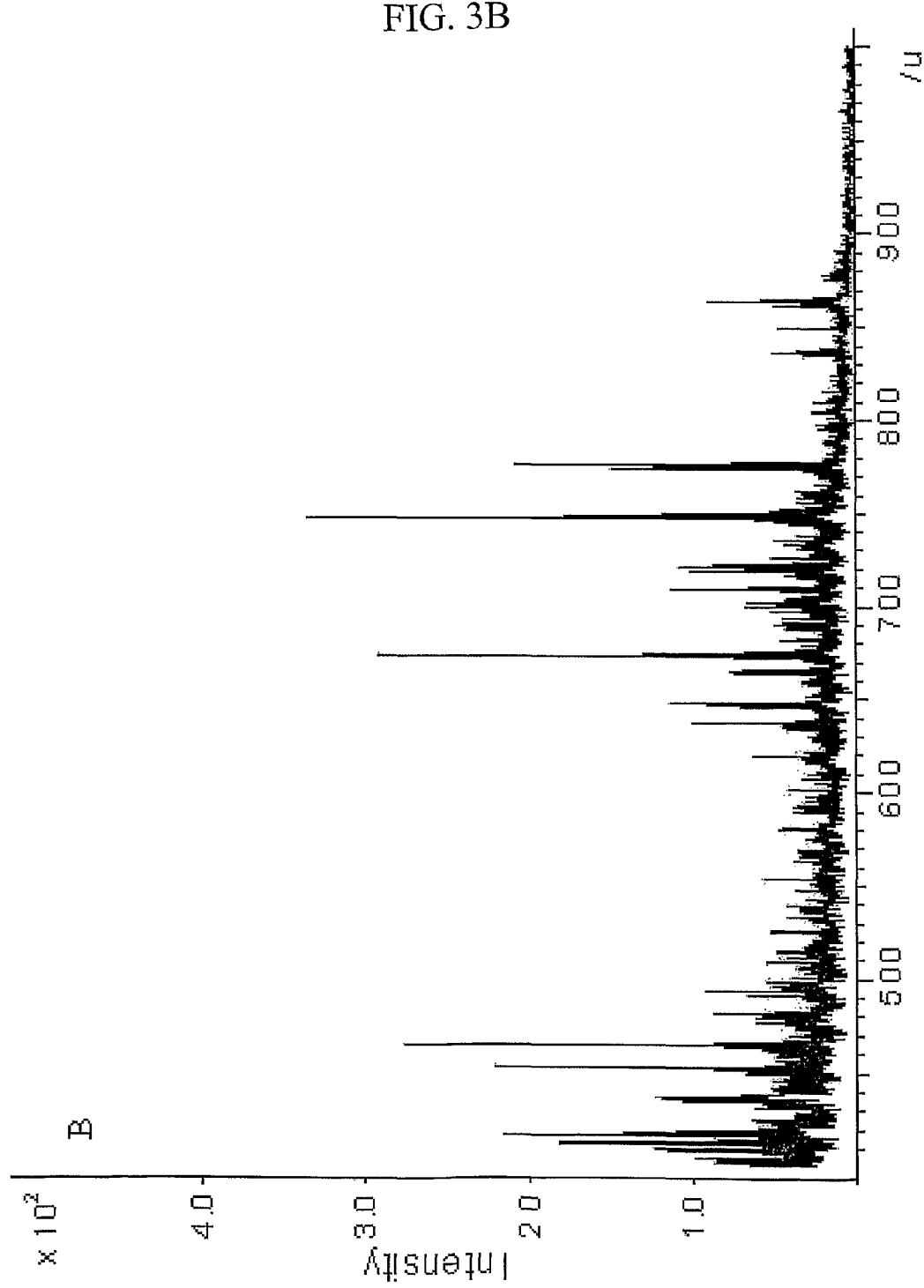

FIG. 3 shows positive (FIG. 3A) and negative (FIG. 3B) TOF-SIMS spectra of a particle spot from one control subject.

Figure 4:
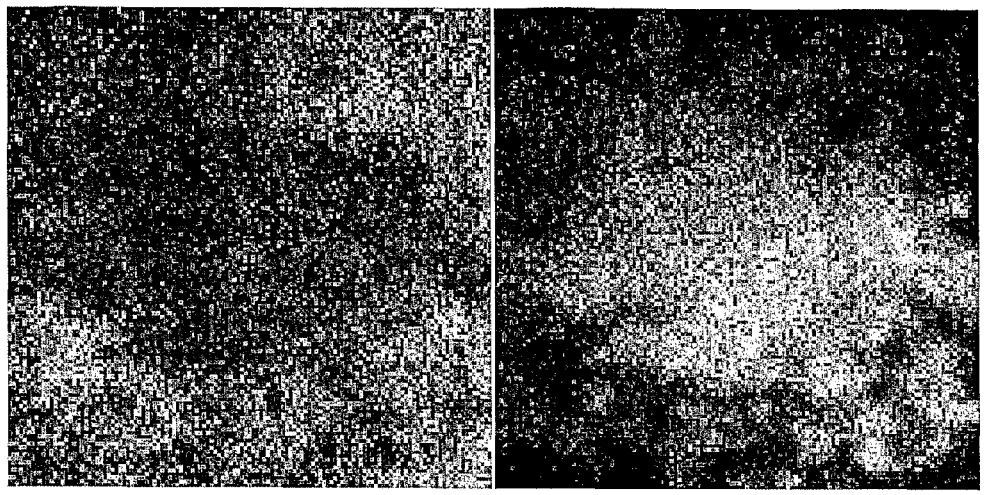
FIG. 4 is a TOF-SIMS image of one spot with exhaled particles from one control subject.

FIG. 4 is a TOF-SIMS image of one spot with exhaled particles from one control subject.

Figure 5:
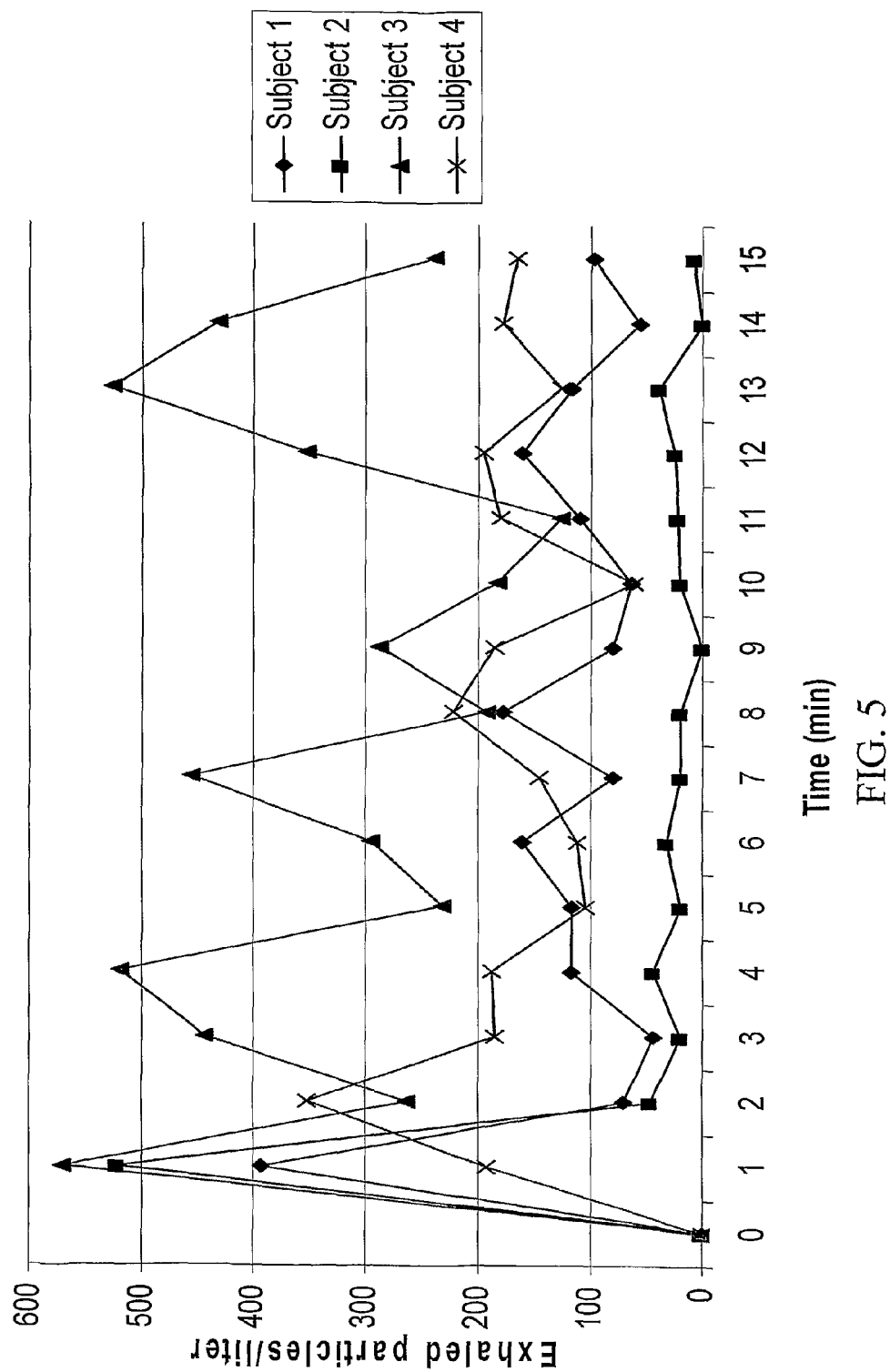
FIG. 5 shows the concentration of exhaled particles (0.5-2.0 μm) vs. time

FIG. 5 shows the concentration of exhaled particles (0.5-2.0 μm) vs. time

Figure 6:
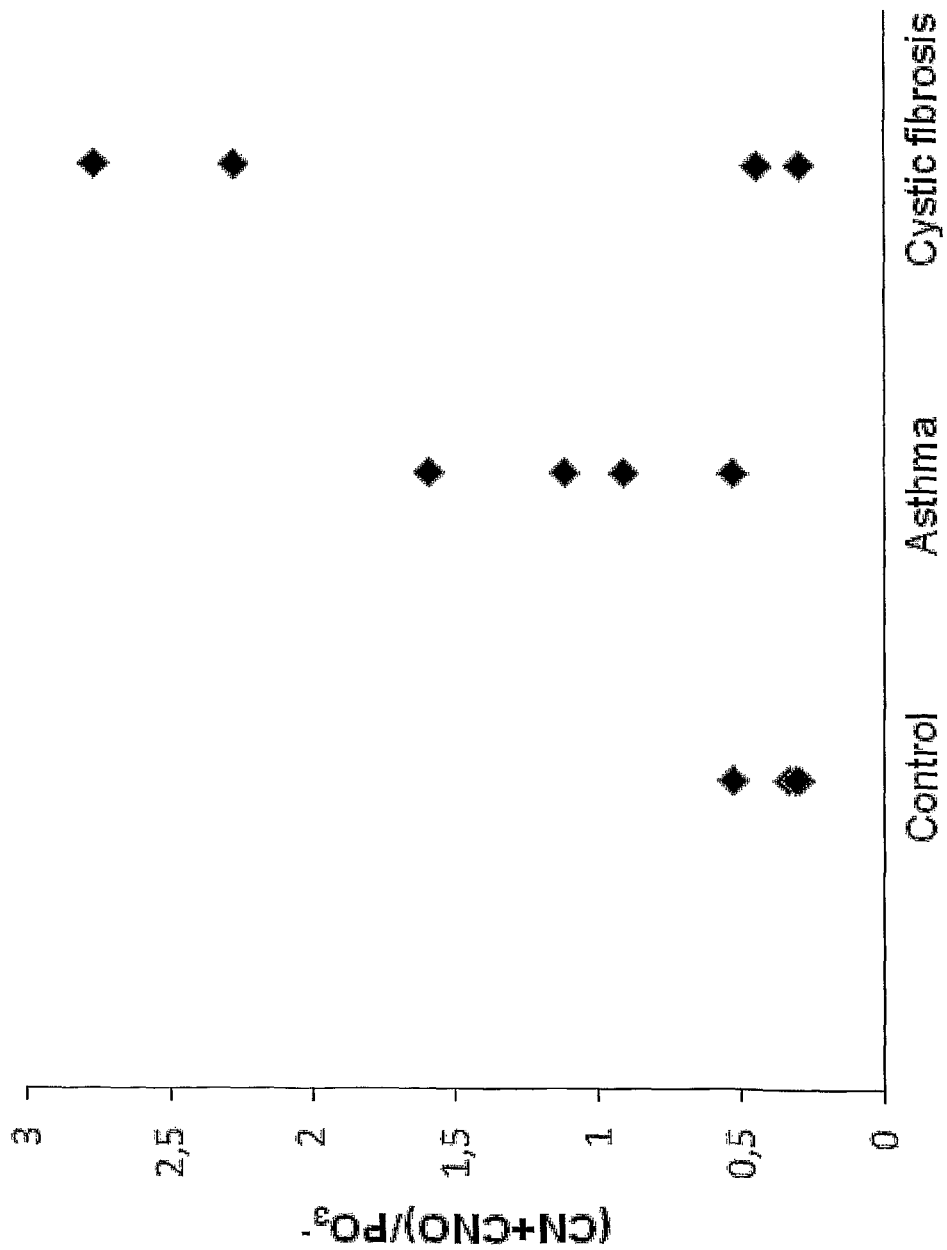
FIG. 6 shows the ratio $(CN+CNO)/PO_3^-$ in a pilot study of healthy subjects and subjects with asthma or cystic fibrosis.

FIG. 6 shows the ration (CN+CNO)/PO$_3$- in a pilot study of healthy subjects and subjects with asthma or cystic fibrosis.

TABLE 1

Assignment of the m/z ratios of peaks of TOF-SIMS spectra of exhaled particles. Molecular species of phospholipids are named as x:a, where x is the number of carbons and a is the number of double bonds:

| Positive ions | | Negative ions | |
|---|---|---|---|
| Assignment | m/z | Assignment | m/z |
| Phosphocholine ion | 184 | C 16:1 | 253 |
| Cholesterol —OH | 369 | C 16:0 | 255 |
| PC fragment | 476 | C 18:1 | 281 |
| PC fragment | 478 | C 18:0 | 283 |
| PC fragment | 494 | PA 32:1 | 645 |
| PC fragment | 522 | PA 32:0 | 647 |
| PC fragment | 524 | PG 28:1 | 663 |
| PC fragment | 650 | PG 28:0 | 665 |
| PC 28:0 + H | 678 | PG 34:2 | 671 |
| PC fragment | 680 | PA 34:1 | 673 |
| PC 30:0 + H | 706 | PG 32:0 | 721 |
| PC 32:1 + H | 732 | PG 34:1 | 747 |
| PC 32:0 + H | 734 | PG 36:2 | 773 |
| PC 34:1 + H | 760 | PG 36:1 | 775 |
| PC 34:0 + H | 762 | PI 34:2 | 833 |
| | | PI 34:1 | 835 |
| | | PI 36:2 | 861 |
| | | PI 36:1 | 863 |

TABLE 2

Total exhaled volume and average concentration of exhaled particles (0.5-2.0 μm) for the 15 minutes sampling period:

| | Subject 1 FEV1 4.1 | | Subject 2 FEV1 2.8 | | Subject 3 FEV1 3.2 | | Subject 4 FEV1 3.2 | |
|---|---|---|---|---|---|---|---|---|
| | Day 1 | Day 2 | Day 1 | Day 2 | Day 1 | Day 2 | Day 1 | Day 2 |
| Volume (liters) | 153 | 128 | 176 | 181 | 142 | 144 | 201 | 166 |
| Particles/liter | 210 | 123 | 149 | 55 | 956 | 343 | 239 | 180 |

Figure 2:
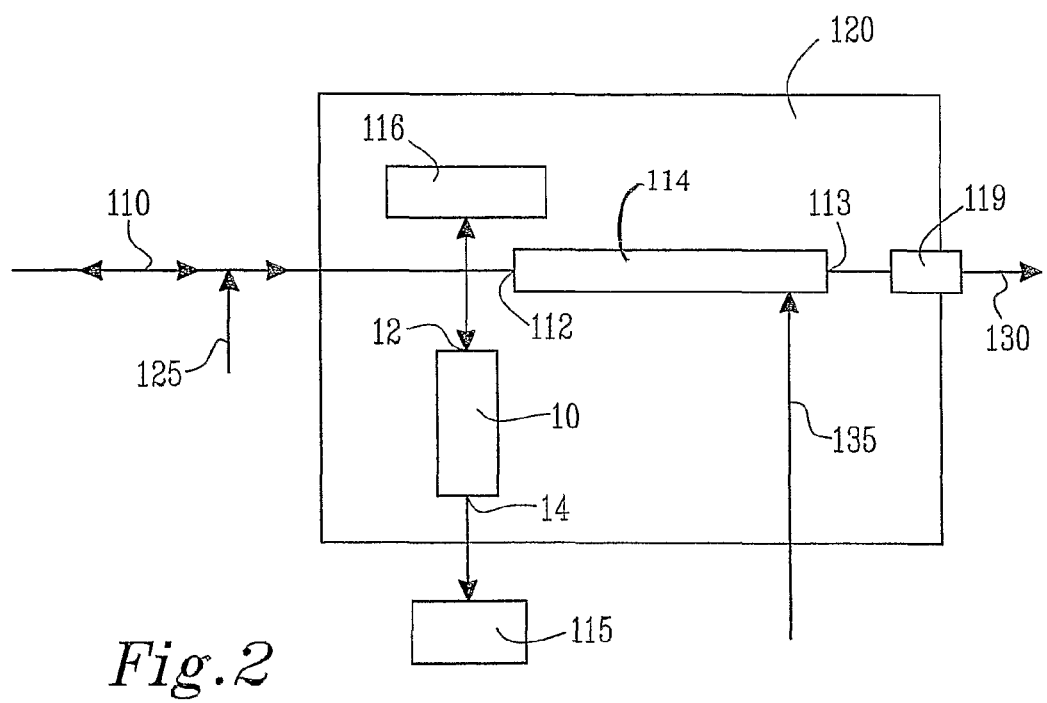
FIG. 2 illustrates system for collection of exhaled particles.

All particle samples gave strong signals from phospholipids (FIGS. 2 and 4 and Table 1). Different species of phosphatidylcholine (PC) were detected as protonated or alkali metal cationized molecular ions in positive mode, while phosphatidylglycerol (PG), phosphatidylinositol (PI) and phosphatidic acid (PA) were detected as deprotonated ions in negative mode, Table 1. The composition of phospholipids was in agreement with that of earlier findings in broncho-alveolar lavage (BAL) fluid indicating that exhaled particles are most likely to derive from the lower airways.

Example 2

The subjects were trained to perform repeated consecutive exhalations corresponding to 80% of their individual maximal forced expired volume in one second (FEV1). Four healthy volunteers, four asthmatics and four patients with cystic fibrosis performed 10 forced exhalations, respectively. Exhaled particles in the size 0.5-2.0 μm were collected on silica wafers. An optical particle counter measured the particle concentration in real-time. Before sampling a washout-period of 3 minutes breathing of particle free air was applied. Silica wafers were analyzed with Time-of-Flight Secondary Ion Mass Spectrometry (TOF-SIMS). Several classes of phospholipids were detected in the particles: phosphatidylcholine (PC), phosphatidylglycerol (PG), phosphatidylinositol (PI) and phosphatidic acid (PA). Some differences were observed between groups. The ratio of the sum of signals of PC and the sum of signals of PG tended to be elevated among asthmatics and patients with cystic fibrosis compared to controls. Also, signals known to be characteristic for proteins and peptides (CNO$^-$) were elevated in comparison to phospholipids in the samples of asthmatics and patients with cystic fibrosis compared to controls (FIG. 6).

Example 3

Subjects performed forced exhalations during 20 minutes. Exhaled particles in the size 0.5-2.0 μm were collected on silica wafers. Silica wafers were stained with a fluorescent reagent, DAPI (4,6-diamidino-2-phenylindole) that binds strongly to DNA and RNA. Strong signals were obtained in the particle spots indicating that exhaled particles contain nucleic acids.

Example 4

Two subjects exhaled 150 L air twice; once for particle collection and once for breath condensate collection. Exhaled particles were desorbed from the sicilica wafers and breath condensate were concentrated before analysis of Surfactant protein A by ELIZA. The total amount of Surfactant protein A (Sp A) were 6 times higher in exhaled particles than those found in exhaled breath condensate, and 4 times higher than that in 100 μL serum. The analysis of Sp A showed high intra-individual reproducibility when tested (CV 5.4 on two subjects when tested at three different occations).

The developed sampling method has high potential for the detection of new biomarkers in exhaled air and monitoring of respiratory disease.

The invention claimed is:

1. A system for collecting and sorting exhaled particles, the system comprising
   a thermostatted compartment,
   a reservoir disposed within the thermostatted compartment, the reservoir comprising a first opening and a second opening;
   a two-way temperature-controlled mouthpiece located outside the thermostatted compartment and connected to the first opening of the reservoir;
   a flow meter disposed within the thermostatted compartment, wherein the flow meter is connected to the second opening of the reservoir, the flow meter discharging gas outside the thermostatted compartment;

means for introducing particle-free humidified air into the reservoir;

an inertial impactor that is disposed within and is removable from the thermostatted compartment, the inertial impactor comprising an inlet that is connected to the first opening of the reservoir;

an outlet; and a plurality of stages arranged such that a primary gas stream comprising particles enters the impactor via the inlet and passes through each stage in turn before exiting the impactor via the outlet;

wherein each of the plurality of stages in the impactor comprises a collection plate oriented perpendicular to the primary gas stream;

is separated from adjacent stages of the plurality of stages by a partition comprising at least one orifice, which directs the primary gas stream towards the collection plate, and wherein the number of orifices, the diameters of the orifices, and the distances between orifices and collection plate in each stage is selected to achieve mass or size segregation of the particles; and a high efficiency particle filter located outside the thermostatted compartment and connected to the mouthpiece, wherein the primary gas stream does not pass through the filter; and a pump located outside the thermostatted compartment and connected to the outlet of the impactor.

2. The system of claim 1, further comprising a particle counter disposed within the thermostatted compartment and connected to the inlet of the impactor.

3. The system of claim 1, further comprising a pump connected to the outlet of the impactor.

4. The system of claim 3, wherein the pump is located outside the thermostatted compartment.

5. The system of claim 1, wherein the surface of at least one collection plate is coated with a hydrophobic substance.

6. The system of claim 1, wherein the surface of at least one collection plate is coated with a hydrophilic substance.

7. The system of claim 1, wherein the surface of at least one collection plate is coated with an antibody.

8. The system of claim 1, wherein the means for introducing particle-free humidified air into the reservoir comprises a third opening in the reservoir.

* * * * *